(12) United States Patent
Palumbo

(10) Patent No.: US 11,896,453 B2
(45) Date of Patent: Feb. 13, 2024

(54) EXTRA ORAL DENTAL VENTILATOR

(71) Applicant: Mark G. Palumbo, Atlantic Beach, NY (US)

(72) Inventor: Mark G. Palumbo, Atlantic Beach, NY (US)

( * ) Notice: Subject to any disclaimer, the term of this patent is extended or adjusted under 35 U.S.C. 154(b) by 482 days.

(21) Appl. No.: 17/009,411

(22) Filed: Sep. 1, 2020

(65) Prior Publication Data

US 2021/0346133 A1     Nov. 11, 2021

Related U.S. Application Data

(60) Provisional application No. 63/022,378, filed on May 8, 2020.

(51) Int. Cl.
*A61C 17/06*     (2006.01)
*A61C 7/06*     (2006.01)

(52) U.S. Cl.
CPC ..................... *A61C 7/06* (2013.01)

(58) Field of Classification Search
CPC ......... A61C 17/06; A61C 17/08; A61C 17/10; A61C 17/12; A61C 19/007; A61C 17/092; A61C 17/096; A61C 17/065; A61B 90/40; A61B 2090/401; A61M 16/009; Y10S 128/91; A61G 13/108
See application file for complete search history.

(56) References Cited

U.S. PATENT DOCUMENTS 3,455,024 A * 7/1969 Gelarie ................ A61C 17/08
                                                     433/93
3,735,491 A * 5/1973 Pabalan, Jr. ........ A61C 17/10
                                                     433/93

(Continued)

FOREIGN PATENT DOCUMENTS

CA      2820948 A1 * 3/2014 ............. A61C 17/08
JP    2008289650 A    12/2008

(Continued)

OTHER PUBLICATIONS

International Search Report of PCT/US2021/031411, dated Aug. 13, 2021.

(Continued)

*Primary Examiner* — Jacqueline T Johanas
*Assistant Examiner* — Shannel Nicole Belk
(74) *Attorney, Agent, or Firm* — Collard & Roe, P.C.; William Collard

(57) ABSTRACT

There is disclosed a dental device configured to be coupled to a vacuum. In at least one embodiment the device comprises at least one channel coupled to the vacuum and in fluid communication with the vacuum. In addition, there can be at least one hood coupled to the channel, and covering the channel wherein the hood is in fluid communication with said at least one channel. In addition, there can be at least one clip coupled to the hood. Furthermore, said at least one clip extending substantially perpendicularly to said at least one hood and substantially parallel to said at least one channel, wherein the vacuum is configured to create a negative pressure inside of said at least one hood, and wherein said at least one clip is configured to couple to a user's mouth, wherein said hood is positioned adjacent to a user's mouth.

21 Claims, 11 Drawing Sheets

(56) References Cited

U.S. PATENT DOCUMENTS

| | | | | |
|---|---|---|---|---|
| 4,446,861 | A | * | 5/1984 | Tada ................ B08B 15/002 |
| | | | | 128/863 |
| 4,865,545 | A | * | 9/1989 | La Rocca ............ A61C 17/08 |
| | | | | 433/96 |
| 5,944,522 | A | | 8/1999 | Lonczak et al. |
| 6,135,770 | A | * | 10/2000 | Bembenek ............ A61C 5/82 |
| | | | | 433/136 |
| 6,308,707 | B1 | * | 10/2001 | Lu ........................ A61G 15/14 |
| | | | | 128/205.27 |
| 6,464,499 | B1 | * | 10/2002 | Lu ........................ A61G 15/14 |
| | | | | 433/91 |
| 8,012,141 | B2 | | 9/2011 | Wright et al. |
| D734,851 | S | | 7/2015 | Nguyen et al. |
| 10,952,831 | B1 | * | 3/2021 | Dürrstein ............ A61C 17/096 |
| 2008/0265565 | A1 | * | 10/2008 | Sitz ...................... F16L 27/093 |
| | | | | 285/98 |
| 2019/0365214 | A1 | * | 12/2019 | Lloro Boada ........ A61B 1/0684 |

FOREIGN PATENT DOCUMENTS

| | | | | |
|---|---|---|---|---|
| JP | 201275703 | A | | 4/2012 |
| WO | WO-8910154 | A1 | * | 11/1989 ............. A61C 17/10 |
| WO | WO-9920201 | A1 | * | 4/1999 ........... A61C 17/043 |

OTHER PUBLICATIONS

Notice of Transmittal of the International Search Report of PCT/US2021/031411, dated Aug. 13, 2021.
Written Opinion of the International Searching Authority of PCT/US2021/031411, dated Aug. 13, 2021.
International Preliminary Report on Patentability in PCT/US2021/031411 dated Nov. 8, 2022.

* cited by examiner

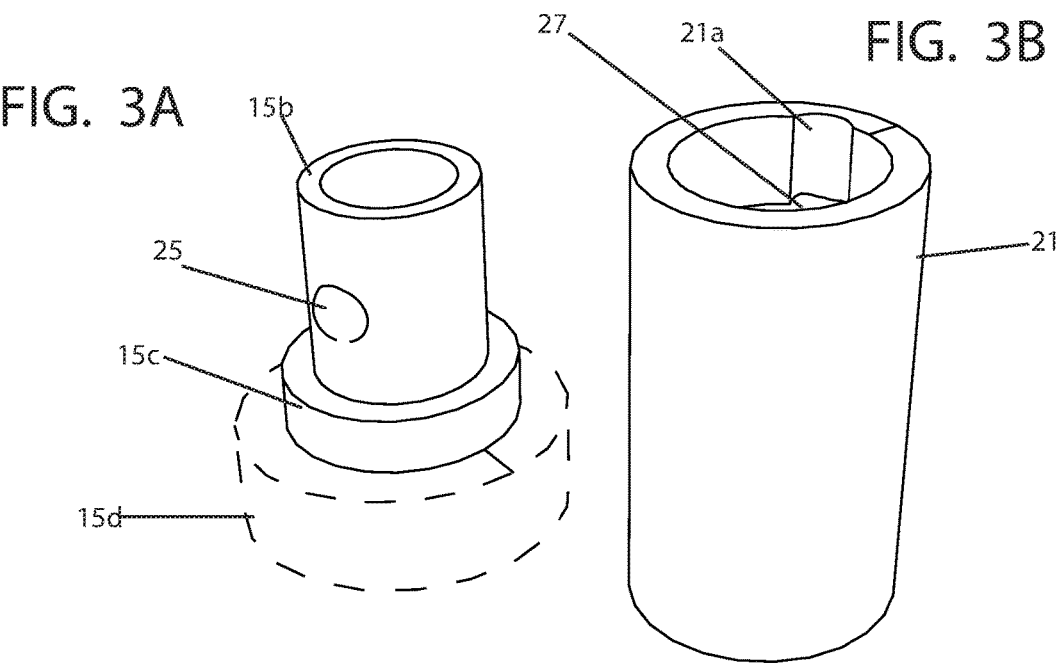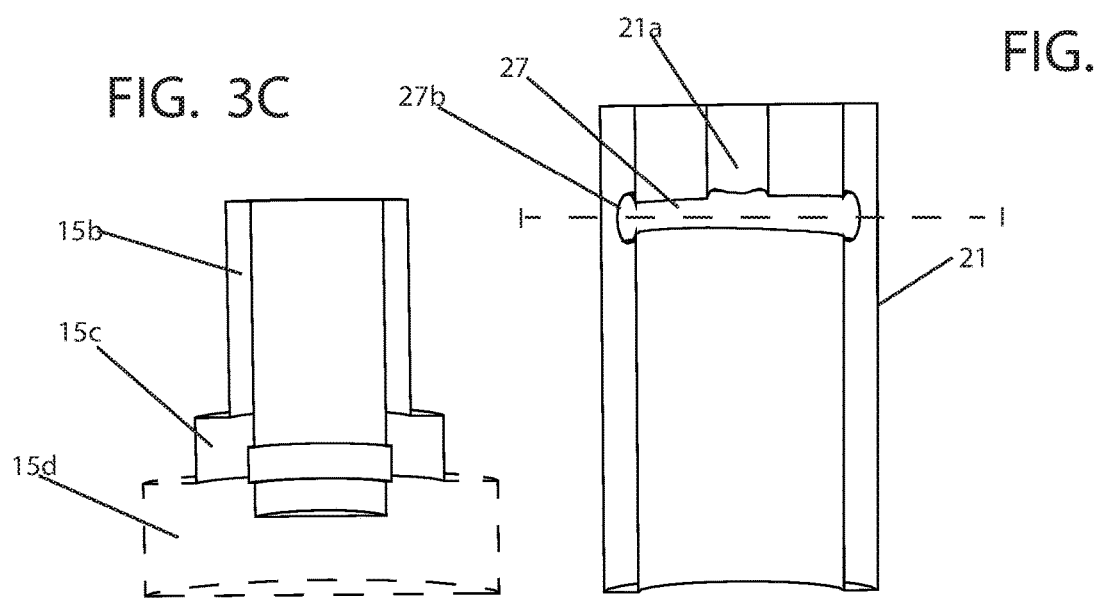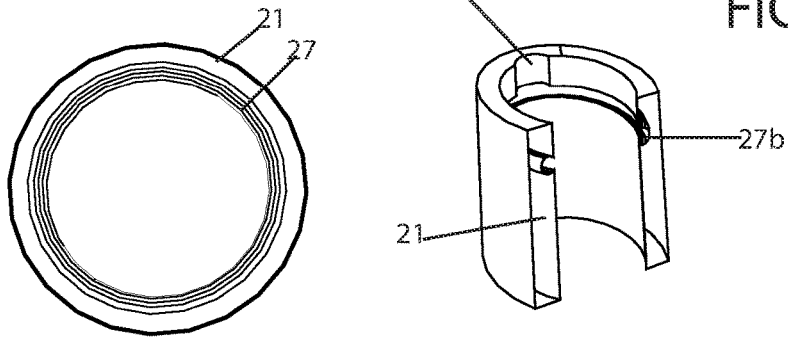

EXTRA ORAL DENTAL VENTILATOR

CROSS REFERENCE TO RELATED APPLICATIONS

This application is a non-provisional application which claims priority from U.S. provisional application Ser. No. 63/022,378 filed on May 8, 2020, the disclosure of which is hereby incorporated by reference in its entirety.

BACKGROUND

The invention relates to a dental aeration and aspiration device. The dental aeration and aspiration device is configured to be placed adjacent to the user's mouth and then configured to be placed adjacent to the user when the user has an open mouth during aerosol and non-aerosol producing events such as a dental prophylaxis or dental restorative procedures.

With the ever present and increasing awareness of respiratory transmitted diseases, there is a need for the removal of potential pathogens utilizing a device that is inexpensive, non-obtrusive and safe for medical and/or dental practitioners. A dental healthcare provider who may need to be within two feet of a patient for an extended period of time would desire to have the treated patients' expirations, fluids within the oral cavity, and/or procedure producing aerosols cleared from the operating field, thereby reducing the exposure to harmful pathogens. Thus, there is a need for an aeration/aspiration device that will simultaneously draw the expirations, fluids from the oral cavity, and aerosols of the treatment field away from the medical or dental practitioner in a safe, secure and efficient manner.

SUMMARY

At least one embodiment of the invention relates to a dental device configured to be coupled to a vacuum. In at least one embodiment the device comprises at least one channel coupled to the vacuum and in fluid communication with the vacuum. In addition, there can be at least one hood coupled to the channel and covering the channel wherein the hood is in fluid communication with said at least one channel.

In addition, there can be at least one clip coupled to the hood. Furthermore, said at least one clip extending substantially perpendicularly to said at least one hood and substantially parallel to said at least one channel, wherein the vacuum is configured to create a negative pressure inside of said at least one hood, and wherein said at least one clip is configured to couple to a user's mouth, wherein said hood is positioned adjacent to a user's mouth.

In at least one embodiment the dental device can comprise at least one additional channel in communication with the first channel.

In at least one embodiment the additional channel is smaller in diameter than the first channel.

In at least one embodiment at least one additional channel extends at least partially inside of the clip.

In at least one embodiment the clip comprises at least two parts comprising a first part and a second part, wherein the second part is disposed at least partially inside of the part of said clip and wherein the second part is slidable inside of said first part thereby forming a telescoping clip that is adjustable in length. In at least one embodiment, the clip can rotate in a substantially 360 degree rotational manner so that the clip can be orientated at any angle vs. the hood.

In at least one embodiment, the hood is semi spherical. Furthermore, in at least one embodiment, the hood is formed substantially clam shell in shape.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 3A is a view of extensible section;

FIG. 3B is a view of an outer frame for receiving the extensible section;

FIG. 3C is a cross-sectional view of the extensible section;

FIG. 3D is a cross-sectional view of the outer frame;

FIG. 3E is a top cross-sectional view of the outer frame taken along line I-I;

FIG. 3F is a perspective cut out view of the outer frame;

DETAILED DESCRIPTION

Figure 1:
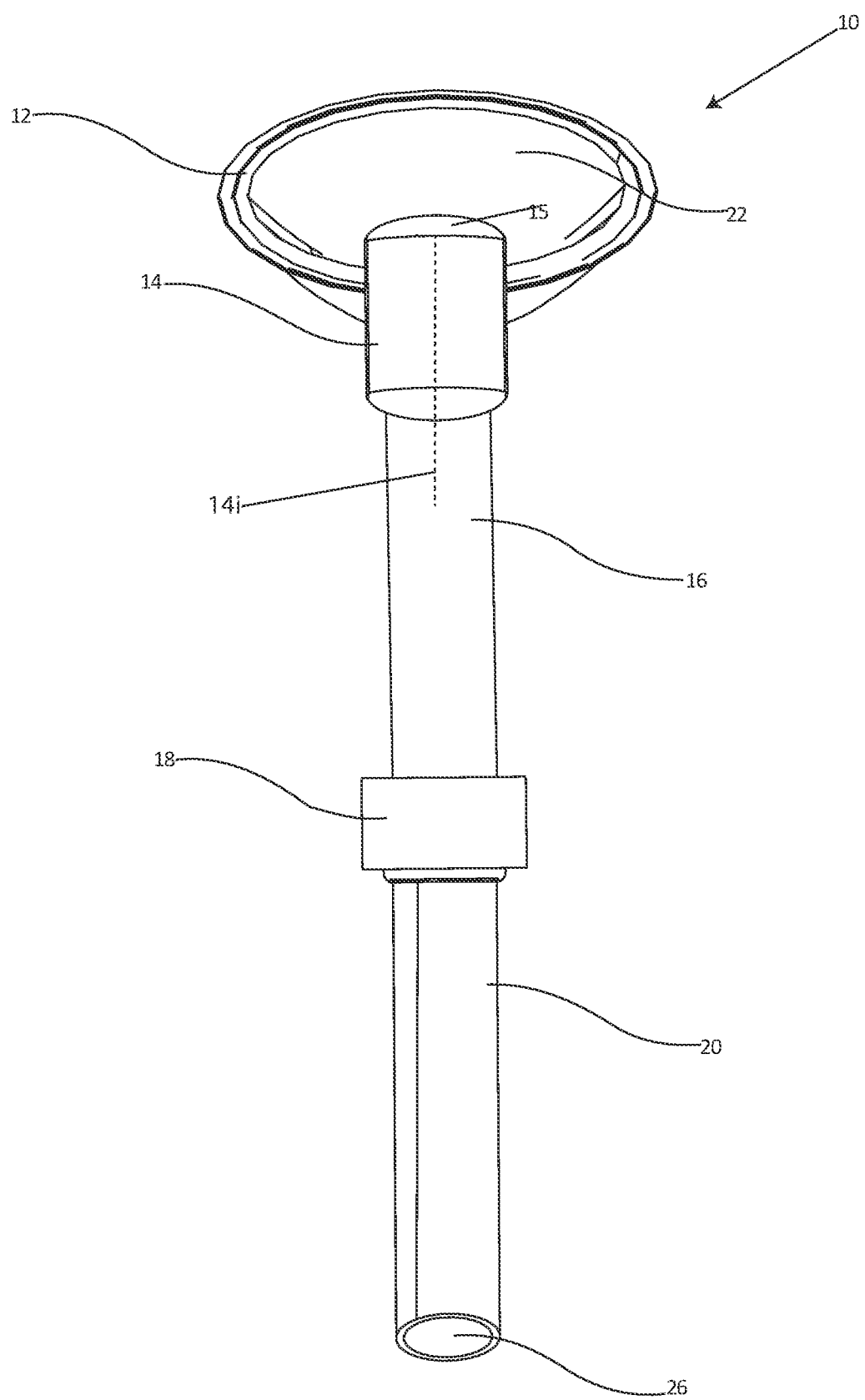
FIG. 1 is a front-bottom perspective view of a first embodiment of a dental device.

FIG. 1 is a front-bottom perspective view of a first embodiment of a dental device 10 which comprises a hood 12, a first shaft 16 and a second shaft 20 wherein the first shaft 16 has a first channel and the second shaft also has a channel or at least one additional channel or contiguous channel.

There is at least one clip 14 which extends substantially perpendicular to an extension of the hood 12. For example, clip 14 has a longitudinal extension 14i which extends substantially transverse to the extension of longitudinal extension 12i of hood 12 (see FIG. 3). There is a cross flange 15 which extends out to clip 14. In addition, extending down from hood 12 is a first shaft 16 which extends down to a rotatable connector 18. Rotatable connector 18 is coupled at a first end to first shaft 16 and at a second end to second shaft 20. Disposed inside of rotatable connector 18 are protrusions 19 and indents 17 (See FIG. 3). Hood 12 includes a hood opening 22 (See FIG. 2) which extends down into a channel which runs through first shaft 16, connector 18, and second shaft 20. A vacuum pump can be connected at the end of shaft 20 so that it creates a vacuum of negative pressure inside of hood 12, hood opening 22, and inside of shaft 16, connector 18, and shaft 20. The hood 12, the shafts 16 and 20 and the clip can be molded, 3D printed, extruded or manufactured in any known way from any suitable material such as plastic, biodegradable materials, such as paper or composites, metal or any other suitable material. In at least one embodiment, the entire device, both body (hood 12 and shafts 16, connector 18 and clip 14, is a plastic intended for single use and disposable. In at least one other embodiment, the body (hood 12 and shafts 16 and 20 and connector 18) is made of a material which is reusable and sterilizable, with the clips 14 being made of a plastic intended for single use and disposable.

Figure 2:
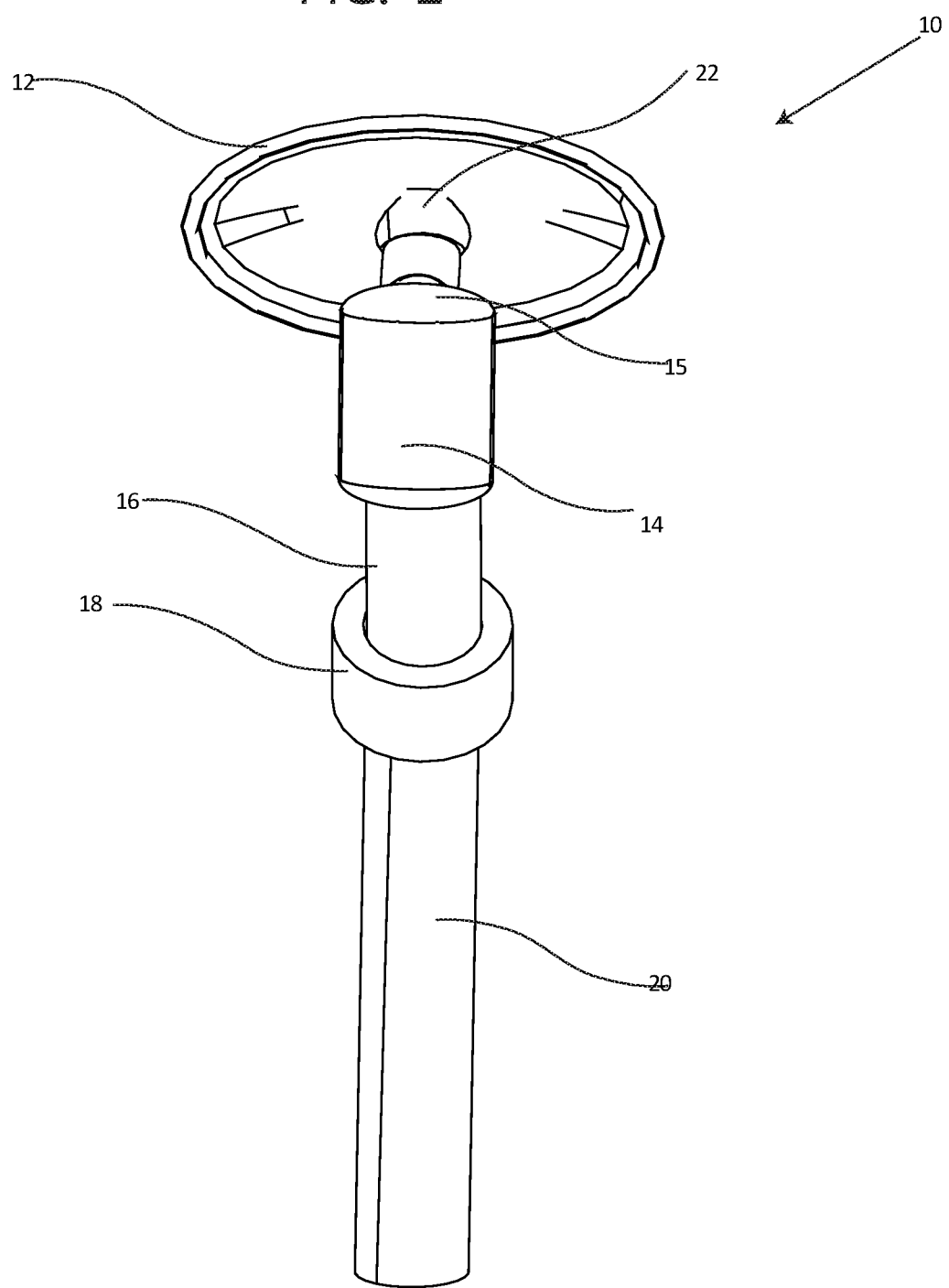
FIG. 2 is a front-top perspective view of the first embodiment of the dental device.

FIG. 2 is a front-top perspective view of the first embodiment of the dental device. Among the different components, there is shown hood 12, hood opening 22, and slots or an outer frame 21 inside of hood 12. Cross flange 15 and clip 14 are also shown along with shafts 16 and 20 and rotatable connector 18.

Figure 3:
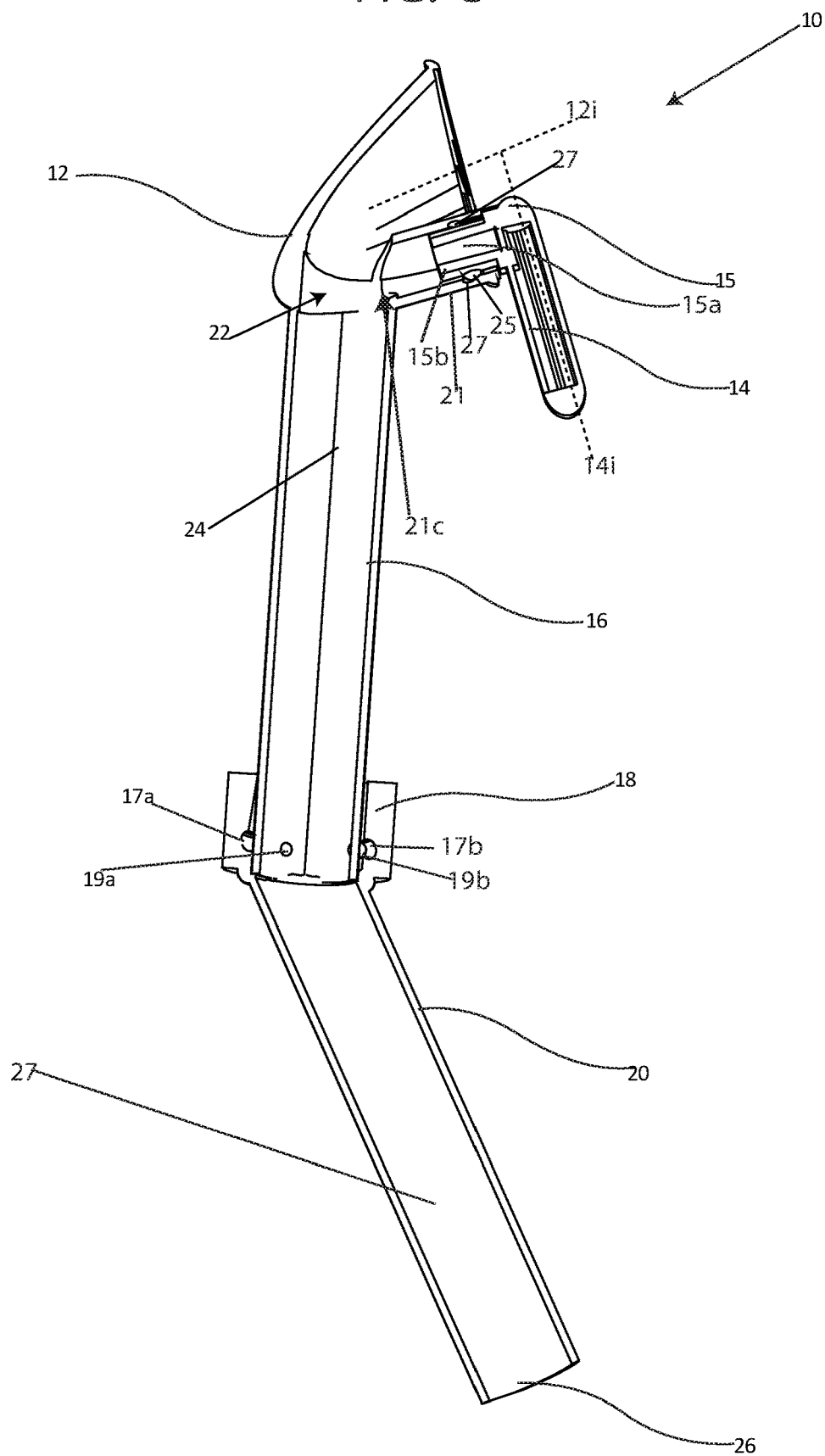
FIG. 3 is a side cross-sectional view of the first embodiment of the dental device.

FIG. 3 is a side cross-sectional view of the first embodiment of the dental device. In this view there is shown hood 12, and longitudinal extension of hood 12i. There is shown cross flange 15, as well as clip 14. Longitudinal line 12i extends along the longitudinal extension of hood 12 and parallel to flange 15. This longitudinal line 12i extends substantially transverse to longitudinal line 14i which extends along clip 14. As shown in this side cross-sectional view, there is shown hood opening 22 which extends down to shaft 16 having opening or channel 24 which forms a channel which extends down to connector 18. This channel 24 is inherent in the cylindrical design of shaft 16, thereby allowing fluid flow such as air to follow through hood 12, through opening 22, into channel 24 in shaft 16 and down into connector 18.

Connector 18 is coupled to and in at least one embodiment directly connected to second shaft 20. First shaft 16 is positioned inside of connector 18 and which has protrusions 19a, and 19b which insert into corresponding indents 17a and 17b Indents 17a and 17b are part of a continuous annular slot disposed within 18 for 19a and 19b to engage with a protrusion. This allows the shaft 16 to be rotatable vs. connector 18 and shaft 20 or alternatively allows collar and shaft 20 to be rotatable vs. first shaft 16. Inside of second shaft 20 is an opening 27 which allows air to flow therethrough and into a vacuum pump. At an end of shaft 20 is an end piece 26.

In addition, clip 14 is coupled to hood 12 via a flange 15 as well as an extensible section 15b. Extensible section 15b has a hollow region 15a. Because of hollow region 15a, extensible section 15b is collapsible inside of an outer frame 21 of hood 12. Coupled to extensible section 15b is protrusion 25 which is configured to insert into indent 27 which is formed as a ring disposed inside of outer frame 21. This allows clip 14 to be inserted into outer frame 21 on hood 12.

As shown in FIGS. 3A-3F, indent 27 is an indent running 360 degrees around the inner aspect of outer frame 21, there is also an indent (27a) starting at and running perpendicular to indent 27, continuous to the outer edge of the outer frame 21. Thus, each of the clips as shown in FIGS. 1-9 can be rotated in an "up" position, protrusion 25 aligns with indent 27a and can be inserted until protrusion 25 meets with indent 27. Once rotated down (into it's functional position), the clip becomes "locked" and engaged. All variations of clips are interchangeable and can be placed, removed, and exchanged as needed.

For example, FIG. 3A is a perspective view of the extensible section 15b which has a protrusion 25, as well as an intermediate base 15c. There is also an optional base 15d which is wider than intermediate base 15c. FIG. 3B is an outer frame 21 having a first slot or indent 21a. There is also another indent or slot 27 which is an annual slot running in a ring inside of outer frame 21.

FIG. 3C shows a cross-sectional view of the extensible section 15b having an intermediate base 15c and base 15d. FIG. 3D is a cross-sectional view of the outer frame having indent or slot 21a as well as annular ring, slot or indent 27 extending around the inner portion of outer frame 21. This slot, ring or indent 27 has a curvature 27b which shows that this slot is rounded so that it is configured to receive protrusion 25 as it engages this slot or ring 27 allowing an associated clip 14, 114, or 214 to be rotated into a desired position.

Additional views of this slot, ring or indent 27 are also shown in FIGS. 3E and 3F which show ring or indent 27, having curvature 27b in outer frame 21 which also has indent or slot 21a as well. The adjustability of the clip 14, 114, and 214, allows for the device to be adjusted in position in a user's mouth so that a more comfortable angle of clip 14, 114, and 214 can be achieved.

Figure 4:
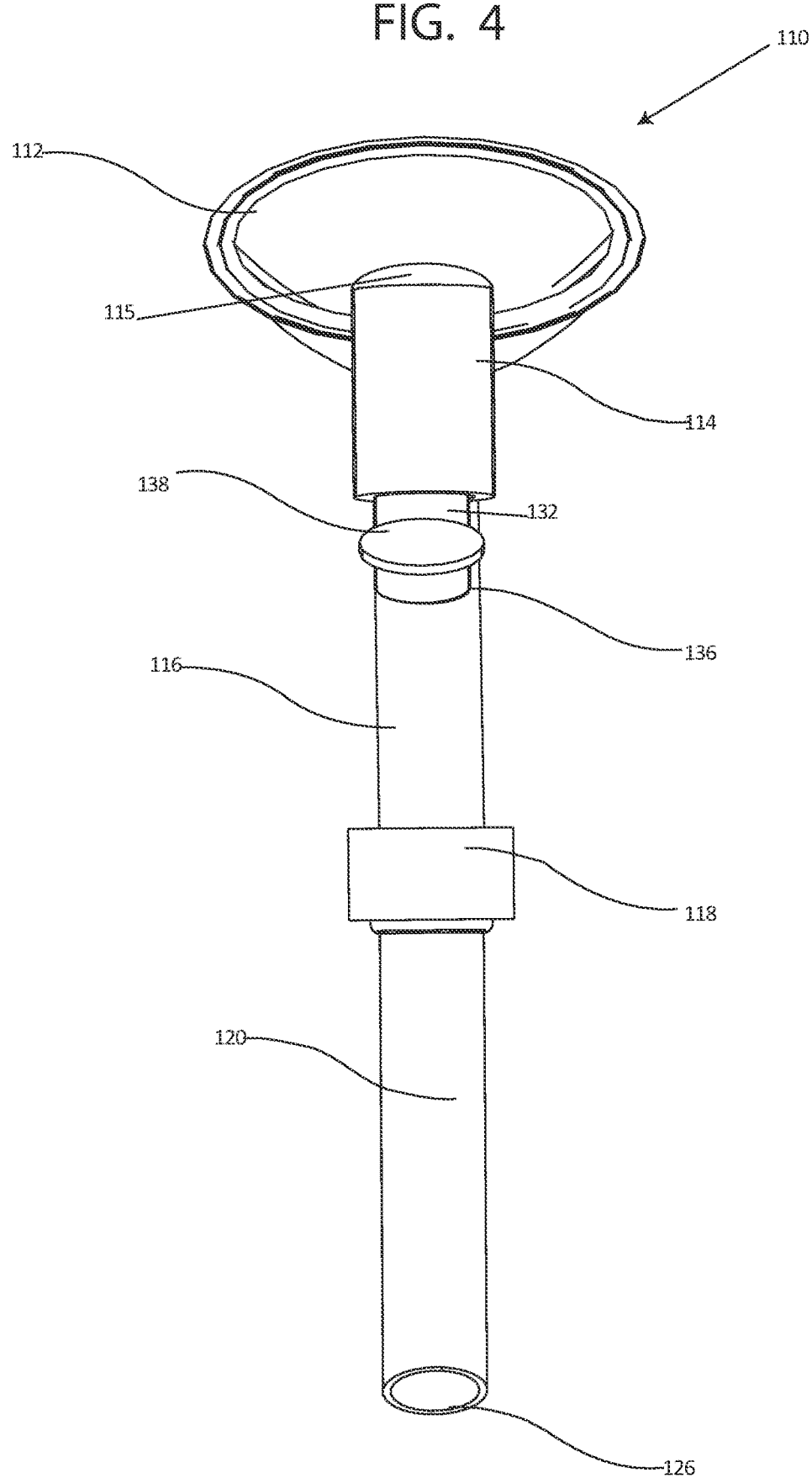
FIG. 4 is a front-bottom perspective view of a second embodiment of a dental device.

FIG. 4 is a front-bottom perspective view of a second embodiment of a dental device 100. The dental device 100 includes a hood 112, and a flange 115 extending out from hood 112. Coupled to flange 115 is a clip 114. In addition, disposed inside of clip 114 is an inner shaft 132 which is telescoping inside of clip 114 so that clip 114 is variable in length. In addition, coupled to shaft 132 is an end flange 138 which extends transverse to the inner shaft 132. First shaft 116 extends down to rotatable connector 118 and is coupled thereto. In addition, rotatable connector 118 is coupled to or connected with second shaft 120. At the bottom of second shaft 120 is an opening 126.

Figure 5:
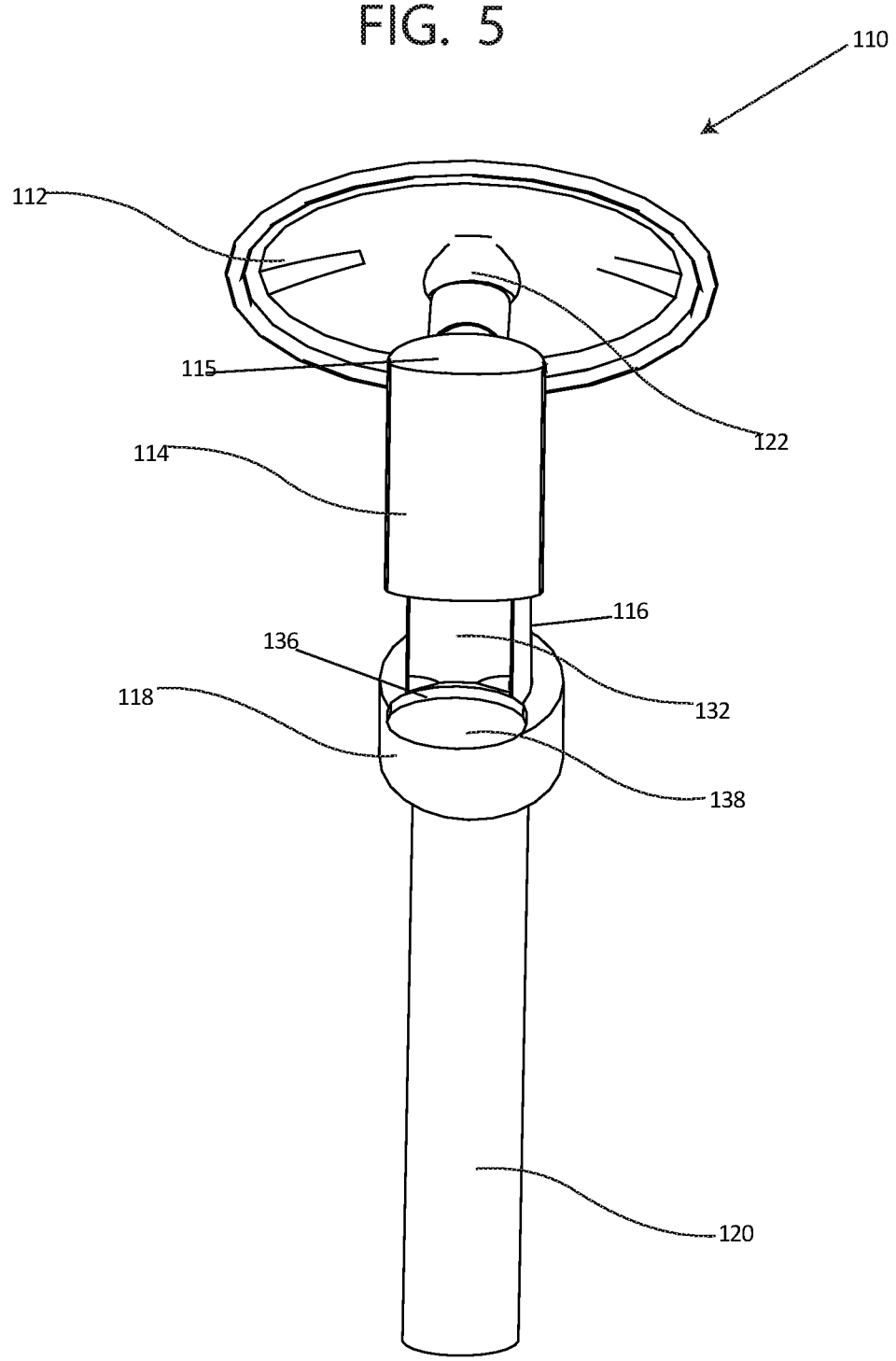
FIG. 5 is a front-top perspective view of the second embodiment of the dental device.

FIG. 5 is a front-top perspective view of the second embodiment of the dental device 110 which shows hood 112, hood opening 122. Extending out from hood 112 is a cross flange 115 which extends substantially perpendicular to clip 114. Adjacent to clip 114 is a shaft 116. In addition, disposed inside of clip 114 is inner shaft 132. Coupled to inner shaft 132 is a transverse shaft 136. In addition, coupled to transverse shaft 136 is an end flange 138.

Furthermore, coupled to shaft 116 is rotatable connector 118. Coupled to rotatable connector 118 is a second shaft 120. Second shaft 120 extends down to a connection with a vacuum to create negative pressure inside of hood 112.

Figure 6:
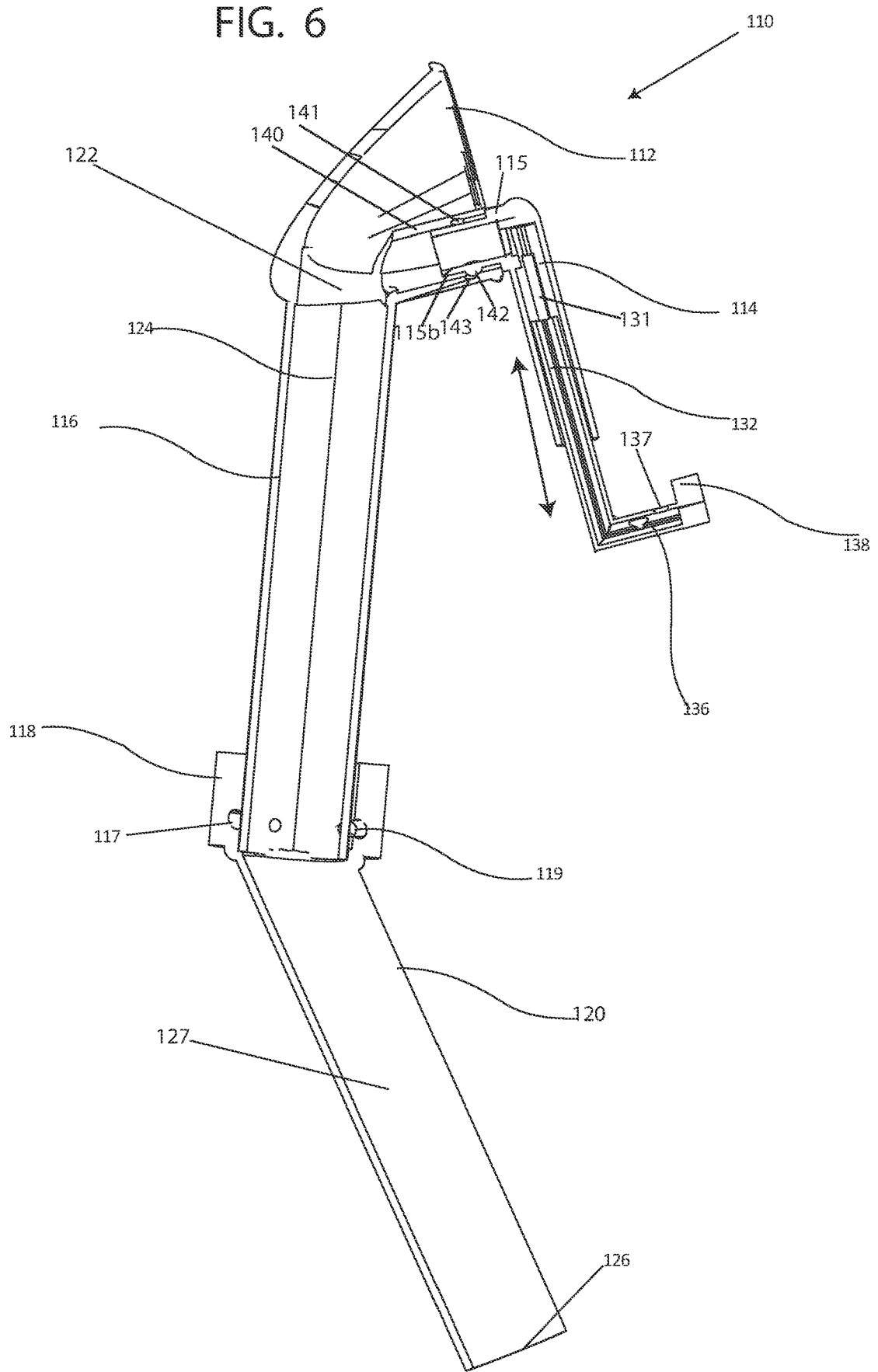
FIG. 6 is a side cross-sectional view of the second embodiment of the dental device.

FIG. 6 is a side cross-sectional view of the second embodiment of the dental device 110. This dental device includes a hood 112 which has a hood opening 122. Hood opening extends into shaft 116. Inside shaft 116 is opening 124 which extends down to opening 127 which is inside of shaft 120. As stated above, shaft 120 is coupled to rotatable coupling 118. Shaft 116 has protrusions 119 while rotatable coupling 118 has indents 117. Thus, the protrusions 119 fit inside of the indents 117. Shaft 120 extends down from coupling or rotatable connector 118 to opening 126 which is configured to be coupled to a vacuum which draws air and creates a negative pressure inside of hood 112 thereby drawing air out of a user's mouth. In addition, this side view shows clip 114 which includes an inner shaft 132 slidable inside of clip 114 along track 131 thereby showing clip 114 is adjustable in length. In addition, shaft 132 extends to transverse shaft 136, which then extends out towards end flange 138. In addition, clip 114 extends along flange 115 inside of channel 140 to connect clip 114 to the body of the device. Channel 140 has indents 141 and 143 configured to receive protrusions 142 allowing the clip 114 to snap therein while still being rotatably adjustable.

Ultimately this embodiment is configured to allow for adjustment of the clip in a substantially vertical manner to allow a further extension of the clip 114 into the user's mouth. The second embodiment is also dual purpose which is capable of aeration or ventilation, as well as aspiration (drawing of fluid out of the user's mouth). Thus, transverse shaft 136 has an opening 137 for receiving fluid such as saliva or aspiration or exhalation therein. This fluid would then travel up shaft 136, through shaft 132 through shaft 115b into opening 122 down through opening 124 in shaft 116, through connector 118 through opening 127 in shaft 120 and down into a vacuum. In addition, flange 138 and the underside of 136 function by design in inhibiting the soft tissue of the oral cavity from obstructing opening 137

Figure 7:
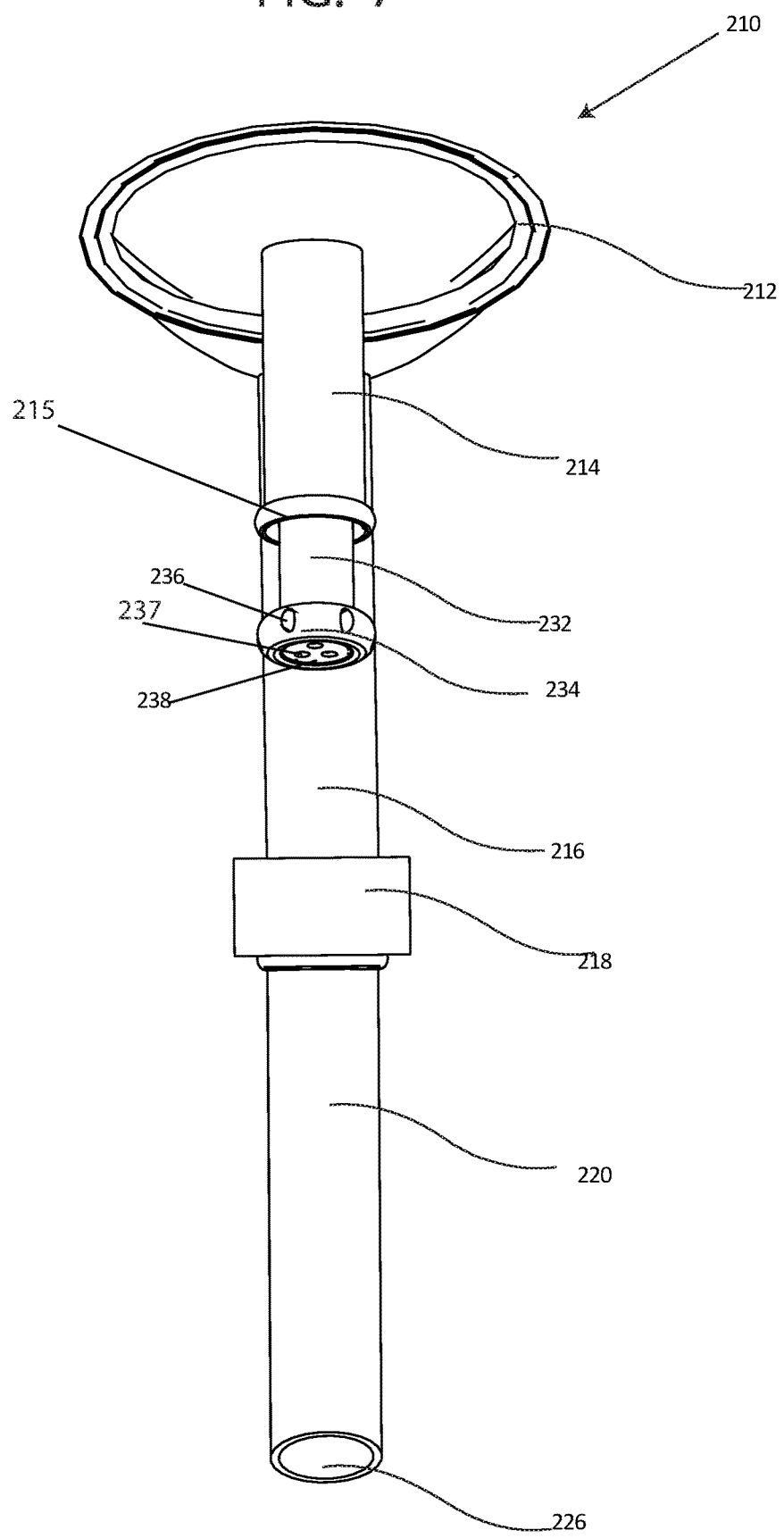
FIG. 7 is a front-bottom perspective view of a third embodiment of a dental device.

FIG. 7 is a front-bottom perspective view of a third embodiment of a dental device 210. This embodiment includes a hood 212, a flange 214 as well as an inner shaft 232. This embodiment is configured so that it is capable of both aeration and aspiration so that it serves a dual purpose.

Thus, in addition, coupled to inner shaft 232 is flange 234 which has holes 236 which is configured to receive fluid from a person's mouth when shaft 232 is inserted into the user's mouth. In addition, there is also an additional interface 238 comprising a plurality of holes 237 which are configured to draw fluid through these holes into shaft 232. In addition, also disclosed in this view are shaft 216 coupled to coupling or rotatable connector 218. Coupling or rotatable connector 218 is also coupled to second shaft 220. At the bottom of second shaft 220 is opening 226 which is configured to be coupled to a vacuum device configured to create a vacuum inside of hood 212.

Figure 8:
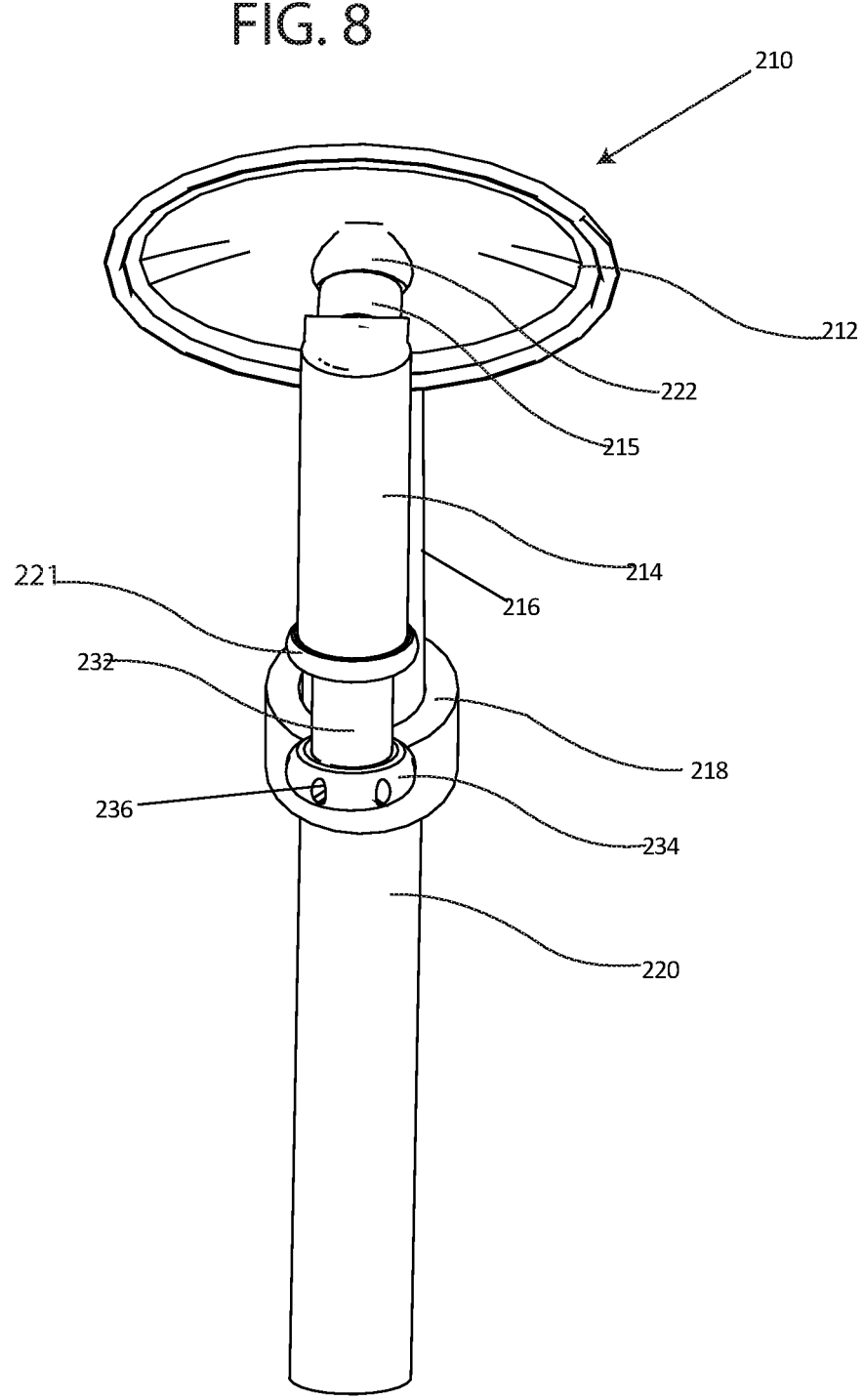
FIG. 8 is a front-top perspective view of the third embodiment of the dental device.

FIG. 8 is a front-top perspective view of the third embodiment of the dental device 210, which discloses a hood 212 having an opening 222. Extending out from hood in a manner substantially coaxial with the longitudinal extension of hood 212 is cross flange 215 which extends in a transverse manner to clip 214. Clip 214 extends substantially coaxial with shaft 216 down to rotatable connector 218. Coupled to rotatable connector 218 is second shaft 220. In addition, as shown, coupled to clip is inner shaft 232 which extends down to flange 234. Disposed in flange 234 are openings or holes 236. Furthermore, there is also shown second shaft 220 which extends down from connector 218.

Figure 9:
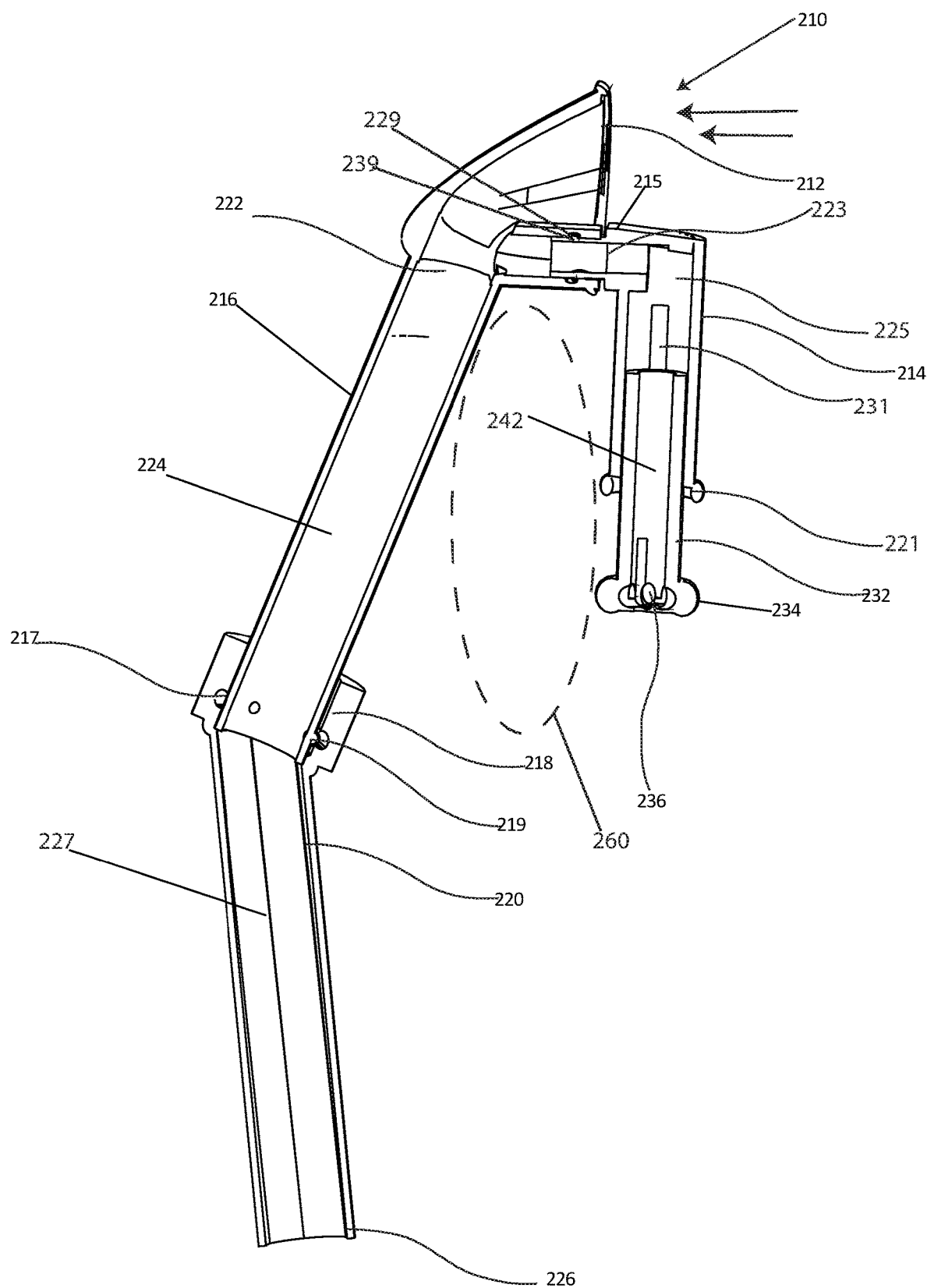
FIG. 9 is a side cross-sectional view of the third embodiment of the dental device.

FIG. 9 is a side cross-sectional view of the third embodiment of the dental device 210 which shows a hood 212 which is configured to receive air expelled from a user as shown by arrows positioned adjacent to the reference numeral 212 of hood 212. This view also shows a side profile of a users' cheek 260 which is configured to receive the clip 214. Clip 214 can be in the form of a flange or a shaft which is configured to extend inside of a user's mouth. Thus, this clip 214 extends down into the user's mouth and is configured to draw air, saliva and other fluids out of the user's mouth. At a first end of clip 214 is a cross flange 215, which has inside of it a channel 223. Channel 223 has at least one outside protrusion 239 which fits inside of a corresponding indent 229 in shaft Inside of clip or shaft is an inner shaft 232 which is slidable along a track 231. Track 231 is coupled to clip 214 and thereby allows inner shaft 232 to slide therein. At the bottom of clip 214 is a ring protrusion 221. In addition, inner shaft 232 has a ring 234 as well. As described above ring 234 has holes 236 disposed therein. Holes 236 and holes 237 (See FIG. 7) are configured to draw saliva, expired respiration and other fluids out of the users' mouth. At the same time hood 212 which has therein a negative pressure or vacuum is configured to draw expired air from the use and into this vacuum. Thus, air is drawn into hood 212 into opening 222, into channel or opening 224, through shaft 216, into channel or opening 227 in shaft 220 and then through opening 226 which is ultimately connected to a vacuum hose. In addition, fluid such as saliva, water or other expired gasses are pulled through holes 236 and 237 into channel 242, into channel 225, through channel 223, into opening 222, through channel or opening 224, through channel or opening 227 and into a corresponding vacuum hose and eventually a vacuum. Thus, this vacuum is creating a consistent state of negative pressure in the different channels in the device to draw the expired gasses from a user as well as other fluids from the user.

Figure 10:
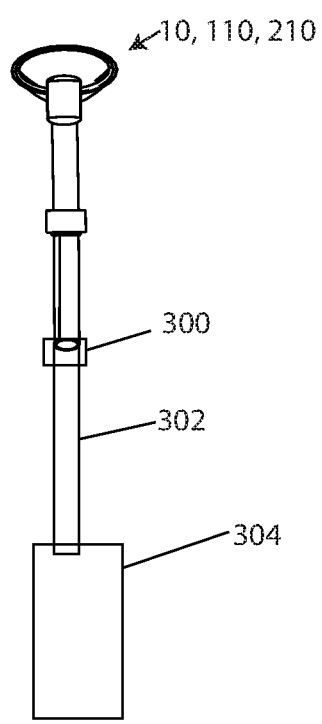
FIG. 10 shows a diagram of a device such as the first embodiment of dental device.

FIG. 10 shows a diagram of a device such as the first embodiment of dental device 10, the second embodiment of a dental device 110 or the third embodiment of the dental device 210 which can be coupled to a coupling 300. Coupling 300 is coupled to a vacuum hose 302 which feeds into a standard dental vacuum 304. This standard dental vacuum is the type of vacuum which is housed in a standard dental office which is currently used to draw fluids from a patient in a dental chair. The coupling 300 is configured as either a clamp coupling or a female coupling configured to receive an end of the shaft such as any one of shaft 20, 120 or 220. Thus, this device is configured to be coupled to a standard HVE (high volume evacuator) fitting attached to a vacuum system that is currently installed in an existing dental office.

As shown in FIGS. 3, 6 and 9 each of the devices comprise separate components that can be releasably snapped together using protrusions and corresponding indents to selectively allow either a coupling or rotatable connector 18, 118, or 218 to be coupled to an associated shaft 16, 116 or 216. Alternatively, an additional set of protrusions and indents form an interface between the clip such as any one of clip 14, 114, and 214 and the body of the corresponding device such as with device 10, 110 or 210. Therefore, this design results in a modular device which has interlocking components which are adjustable and can be releasably connected to each other.

What is claimed is:

1. A dental device configured to be coupled to a vacuum comprising:
   a) at least one channel coupled to the vacuum and in fluid communication with the vacuum;
   b) at least one hood coupled to said at least one channel, and covering said at least one channel wherein said hood is in fluid communication with said at least one channel; and
   c) at least one clip coupled to said at least one hood, said at least one clip positioned such that said at least one clip and said at least one channel are configured to support said at least one hood above a user's cheek, wherein said clip is in fluid communication with said at least one hood and said at least one channel and wherein the vacuum is configured to create a negative pressure inside of said channel, said at least one hood and said clip, and wherein said at least one clip is configured to couple to a user's mouth, wherein said hood is configured to be positioned adjacent to a user's mouth, outside of the user's mouth, and above a user's cheek, and wherein said clip is configured to extend inside of a user's mouth.

2. The dental device as in claim 1, further comprising at least one additional channel in communication with said at least one channel.

3. The dental device as in claim 2, wherein said at least one additional channel is smaller in diameter than said at least one channel.

4. The dental device as in claim 2, wherein said at least one additional channel extends at least partially inside of said at least one clip.

5. The dental device as in claim 1, wherein said at least one clip comprises at least two parts comprising a first part and a second part, wherein said second part is disposed at least partially inside of said first part of said clip and wherein said second part is slidable inside of said first part forming a telescoping clip that is adjustable in length and selectively extend a pre-set length inside of a user's mouth.

6. The dental device as in claim 1, wherein said at least one hood is semi spherical.

7. The dental device as in claim 2, wherein said additional channel is disposed in said clip.

8. The dental device as in claim 7, wherein said clip further comprises at least one hole for receiving fluid therein.

9. The dental device as in claim 1, wherein said at least one clip is rotatable.

10. The dental device as in claim 7, wherein said at least one clip is a telescoping clip having at least two shafts, comprising at least one inner shaft and at least one outer shaft, wherein said at least one inner shaft is slidable inside of said at least one outer shaft.

11. The dental device as in claim 10, wherein said at least one inner shaft and said at least one outer shaft are each hollow cylinders.

12. The dental device as in claim 11, wherein said at least one clip has a plurality of holes disposed in an end region of said at least one clip.

13. The dental device as in claim 12, wherein said plurality of holes comprises at least one hole of a first face of said clip and at least one hole on a second face of said at least one clip.

14. The dental device as in claim 1, wherein said clip is coupled to said hood via at least one intermediate shaft extending substantially perpendicular to said clip.

15. The dental device as in claim 1, wherein said channel comprises at least two channels comprising at least a first channel and a second channel coupled together with at least one coupling.

16. The dental device as in claim 15, wherein said at least one coupling is a rotatable coupling wherein said first channel and said second channel are rotatable with respect to each other and wherein said hood is coupled to said first channel so that said hood is rotatable with respect to said second channel.

17. The dental device as in claim 16, wherein said first channel and said second channel intersect each other at an angle offset from a straight line.

18. The dental device as in claim 17, wherein said at least one coupling comprises at least one protrusion coupled to said first channel and at least one indent coupled to said second channel wherein said at least one protrusion is slidable inside of said indent on said second channel.

19. The dental device as in claim 1, wherein said at least one channel comprises only one channel and is configured to evacuate said hood and said at least one clip.

20. The dental device as in claim 1, wherein said clip, said hood, and channel are configured so that when said clip is positioned inside of a user's mouth, said channel is positioned outside of said user's mouth adjacent to a user's cheek thereby securing said hood above a user's mouth when said clip is positioned on one side of a user's cheek and the channel being on an opposite side of the user's cheek.

21. A dental device configured to be coupled to a vacuum comprising:
 a) at least one channel coupled to the vacuum and in fluid communication with the vacuum;
 b) at least one hood coupled to said at least one channel, and covering said at least one channel wherein said hood is in fluid communication with said at least one channel; and
 c) at least one clip coupled to said at least one hood, wherein said clip is in fluid communication with said at least one hood and said at least one channel and wherein the vacuum is configured to create a negative pressure inside of said channel, said at least one hood and said clip, and wherein said clip, said hood, and said channel are configured so that when said clip is positioned inside of a user's mouth, said channel is positioned outside of said user's mouth adjacent to a user's cheek thereby securing said hood above a user's mouth when said clip is positioned on one side of a user's cheek and the channel being positioned on an opposite side of the user's cheek.

* * * * *